(12) United States Patent
Machida

(10) Patent No.: US 10,736,591 B2
(45) Date of Patent: Aug. 11, 2020

(54) CONTROL DEVICE, CONTROL METHOD, AND PROGRAM

(71) Applicant: CANON KABUSHIKI KAISHA, Tokyo (JP)

(72) Inventor: Yoshihito Machida, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 347 days.

(21) Appl. No.: 15/034,795

(22) PCT Filed: Oct. 30, 2014

(86) PCT No.: PCT/JP2014/078866
§ 371 (c)(1),
(2) Date: May 5, 2016

(87) PCT Pub. No.: WO2015/068631
PCT Pub. Date: May 14, 2015

(65) Prior Publication Data
US 2016/0270750 A1    Sep. 22, 2016

(30) Foreign Application Priority Data

Nov. 8, 2013    (JP) ................................. 2013-232310

(51) Int. Cl.
*A61B 6/00*   (2006.01)
*A61B 6/04*   (2006.01)

(52) U.S. Cl.
CPC ............ *A61B 6/486* (2013.01); *A61B 6/0492* (2013.01); *A61B 6/5205* (2013.01);
(Continued)

(58) Field of Classification Search
CPC ..... A61B 6/486; A61B 6/5205; A61B 6/5235; G06T 2207/10121; G06T 7/0016
See application file for complete search history.

(56) References Cited

U.S. PATENT DOCUMENTS 4,870,692 A * 9/1989 Zuiderveld ........... G06T 3/4007
                                                        382/107
6,295,336 B1 * 9/2001 Aach ...................... A61B 6/542
                                                        378/108
(Continued)

FOREIGN PATENT DOCUMENTS

JP    4-010790 A    1/1992
JP    6-225869 A    8/1994
(Continued)

*Primary Examiner* — David J Makiya
*Assistant Examiner* — Soorena Kefayati
(74) *Attorney, Agent, or Firm* — Canon U.S.A., Inc. IP Division

(57) ABSTRACT

A control device includes a unit that specifies, among a plurality of pieces of image data generated by detection means in accordance with a detection result of radiated rays that have passed through a subject, the amount of change in a relative position of the subject with respect to the detection means during a period from a generation timing of immediately preceding image data, which is generated immediately before target image data, to a generation timing of the target image data, a unit that sets the amount of radiated rays with which irradiation means performs irradiation in accordance with the amount of change, a unit that determines a composition ratio in accordance with the amount of change, and a unit that reduces noise of the target image data by combining, in accordance with the composition ratio, image data generated before the target image data with the target image data.

13 Claims, 5 Drawing Sheets

(52) U.S. Cl.
CPC .......... *A61B 6/5235* (2013.01); *A61B 6/5264* (2013.01); *A61B 6/54* (2013.01)

(56) References Cited

U.S. PATENT DOCUMENTS

| | | | | |
|---|---|---|---|---|
| 8,050,509 | B2* | 11/2011 | Jeong | G06K 9/40 |
| | | | | 382/254 |
| 8,594,271 | B2* | 11/2013 | Sakaguchi | G06T 7/11 |
| | | | | 378/4 |
| 9,801,602 | B2* | 10/2017 | Nagae | A61B 6/5205 |
| 2005/0111614 | A1* | 5/2005 | Matsuura | A61B 6/032 |
| | | | | 378/19 |
| 2007/0071171 | A1* | 3/2007 | Hayashida | A61B 6/00 |
| | | | | 378/98 |
| 2008/0103834 | A1* | 5/2008 | Reiner | G16H 70/20 |
| | | | | 705/3 |
| 2009/0169080 | A1* | 7/2009 | Noordhoek | G06T 5/003 |
| | | | | 382/131 |
| 2009/0202129 | A1* | 8/2009 | Omi | G06K 9/40 |
| | | | | 382/132 |
| 2009/0285468 | A1* | 11/2009 | Omi | G06T 5/50 |
| | | | | 382/132 |
| 2010/0104167 | A1* | 4/2010 | Sakaguchi | G06T 7/11 |
| | | | | 382/132 |
| 2010/0142792 | A1* | 6/2010 | Sakaguchi | A61B 6/00 |
| | | | | 382/132 |
| 2010/0232573 | A1* | 9/2010 | Ozawa | A61B 6/04 |
| | | | | 378/95 |
| 2011/0069175 | A1* | 3/2011 | Mistretta | G06T 5/50 |
| | | | | 348/164 |
| 2011/0129059 | A1* | 6/2011 | Kobayashi | A61B 6/032 |
| | | | | 378/8 |
| 2012/0163534 | A1* | 6/2012 | Nambu | A61B 6/12 |
| | | | | 378/44 |
| 2012/0201351 | A1* | 8/2012 | Iwakiri | A61B 6/4283 |
| | | | | 378/62 |
| 2012/0312961 | A1* | 12/2012 | Raleigh | A61B 6/12 |
| | | | | 250/206 |
| 2014/0051991 | A1* | 2/2014 | Sakaguchi | A61B 6/4441 |
| | | | | 600/424 |
| 2014/0093043 | A1* | 4/2014 | Nakatsugawa | A61B 6/481 |
| | | | | 378/62 |
| 2014/0110595 | A1* | 4/2014 | Iwakiri | A61B 6/4233 |
| | | | | 250/394 |
| 2014/0153842 | A1* | 6/2014 | Pescatore | G06T 5/002 |
| | | | | 382/264 |
| 2014/0193082 | A1* | 7/2014 | Ohnuki | H04N 1/409 |
| | | | | 382/205 |
| 2014/0343344 | A1* | 11/2014 | Saunders | A61N 5/107 |
| | | | | 600/1 |
| 2015/0098550 | A1* | 4/2015 | Yi | A61B 6/5205 |
| | | | | 378/62 |
| 2015/0139394 | A1* | 5/2015 | Kang | A61B 6/5211 |
| | | | | 378/62 |
| 2015/0139395 | A1* | 5/2015 | Yi | G01N 23/04 |
| | | | | 378/62 |
| 2015/0356756 | A1* | 12/2015 | Okamoto | A61B 6/032 |
| | | | | 382/131 |
| 2015/0363926 | A1* | 12/2015 | Enomoto | A61B 6/4233 |
| | | | | 382/132 |
| 2016/0232648 | A1* | 8/2016 | Bertens | G06T 5/002 |

FOREIGN PATENT DOCUMENTS

| | | |
|---|---|---|
| JP | 8-55696 A | 2/1996 |
| JP | 2000-244817 A | 9/2000 |
| JP | 3162446 B2 | 4/2001 |
| JP | 3400063 B2 | 4/2003 |
| JP | 2008-119195 A | 5/2008 |
| JP | 2010-131371 A | 6/2010 |
| JP | 2012-161530 A | 8/2012 |

* cited by examiner (a)

(b)

(c)

| FRAME NUMBER | 1 | 2 | 3 | 4 | 5 | 6 | 7 |
|---|---|---|---|---|---|---|---|
| AMOUNT OF CHANGE IN POSITION [mm] | 50 | 100 | 100 | 50 | 0 | 0 | 0 |
| AMOUNT-OF-X-RAYS SETTING VALUE [μGy] | 2 | 2 | 2 | 2 | 1 | 1 | 1 |

| FRAME NUMBER | 1 | 2 | 3 | 4 | 5 | 6 | 7 |
|---|---|---|---|---|---|---|---|
| AMOUNT OF CHANGE IN POSITION [mm] | 50 | 100 | 100 | 50 | 0 | 0 | 0 |
| RECURSIVE FILTER COEFFICIENT | 0.8 | 0.9 | 0.9 | 0.8 | 0.5 | 0.5 | 0.5 |

| FRAME NUMBER | 1 | 2 | 3 | 4 | 5 | 6 | 7 |
|---|---|---|---|---|---|---|---|
| AMOUNT OF CHANGE IN POSITION [mm] | 50 | 100 | 100 | 50 | 0 | 0 | 0 |
| AMOUNT-OF-X-RAYS SETTING VALUE [μGy] | 1 | 1 | 1 | 1 | 2 | 1 | 1 |

FIG. 9

| FRAME NUMBER | 1 | 2 | 3 | 4 | 5 | 6 | 7 |
|---|---|---|---|---|---|---|---|
| AMOUNT OF CHANGE IN POSITION [mm] | 50 | 100 | 100 | 50 | 0 | 0 | 0 |
| RECURSIVE FILTER COEFFICIENT | 1 | 1 | 1 | 1 | 1 | 1 | 0.5 |

FIG. 10

| FRAME NUMBER | 1 | 2 | 3 | 4 | 5 | 6 | 7 |
|---|---|---|---|---|---|---|---|
| AMOUNT OF CHANGE IN POSITION [mm] | 50 | 100 | 100 | 50 | 0 | 0 | 0 |
| AMOUNT-OF-X-RAYS SETTING VALUE [µGy] | 1 | 1 | 1 | 1 | 2 | 1 | 1 |

CONTROL DEVICE, CONTROL METHOD, AND PROGRAM

TECHNICAL FIELD

The disclosure of the present specification relates to a control device, a control method, and a program for radiation imaging.

BACKGROUND ART

Unlike in general imaging, a fluoroscope is used not only for examinations but also for a technique called IVR in which an intravascular treatment and the like are performed while a fluoroscopic image is being observed. When such a technique is performed, a fluoroscopy time becomes longer in accordance with the difficulty or the like of the technique, which may result in a case where the amount of radiated rays to which a patient is exposed is increased. As a technology for reducing the amount of radiated rays to which a patient is exposed like this, for example, PTL 1 discloses a technology in which an exposure amount of radiated rays is reduced by changing a pulse duty factor in accordance with the motion or the like of a table. In addition, PTL 2 discloses a technology in which an irradiation pattern acquired by combining irradiation using a normal amount of rays and irradiation using an amount of rays smaller than the normal amount of rays is repeated.

CITATION LIST

Patent Literature

PTL 1: Japanese Patent Laid-Open No. 8-55696
PTL 2: Japanese Patent Laid-Open No. 2008-119195

SUMMARY OF INVENTION

Technical Problem

However, in the case where a pulse duty factor is reduced, the smoothness of motion may be insufficient, and in the case where the amount of radiated rays is reduced, there is a problem in that the amount of noise may be increased.

Solution to Problem

A control device according to an embodiment of the present invention includes amount-of-change specifying means that specifies, among a plurality of pieces of image data generated by detection means in accordance with a detection result of radiated rays that have passed through a subject, the amount of change in a relative position of the subject with respect to the detection means during a period from a generation timing of immediately preceding image data, which is generated immediately before target image data, to a generation timing of the target image data, amount-of-radiated-rays setting means that sets the amount of radiated rays with which irradiation means performs irradiation in accordance with the amount of change, composition ratio determination means that determines a composition ratio in accordance with the amount of change, and noise reduction means that reduces noise of the target image data by combining, in accordance with the composition ratio, image data generated before the target image data with the target image data.

Advantageous Effects of Invention

As a result, high-quality image data may be acquired, while the amount of radiated rays to which a patient is exposed is reduced.

BRIEF DESCRIPTION OF DRAWINGS

FIG. 9 is a diagram illustrating a recursive filter coefficient.
FIG. 10 is a diagram illustrating amount-of-X-rays setting values.

DESCRIPTION OF EMBODIMENTS

In the following, embodiments of the present invention will be described in accordance with the drawings.

First Embodiment

Figure 1:
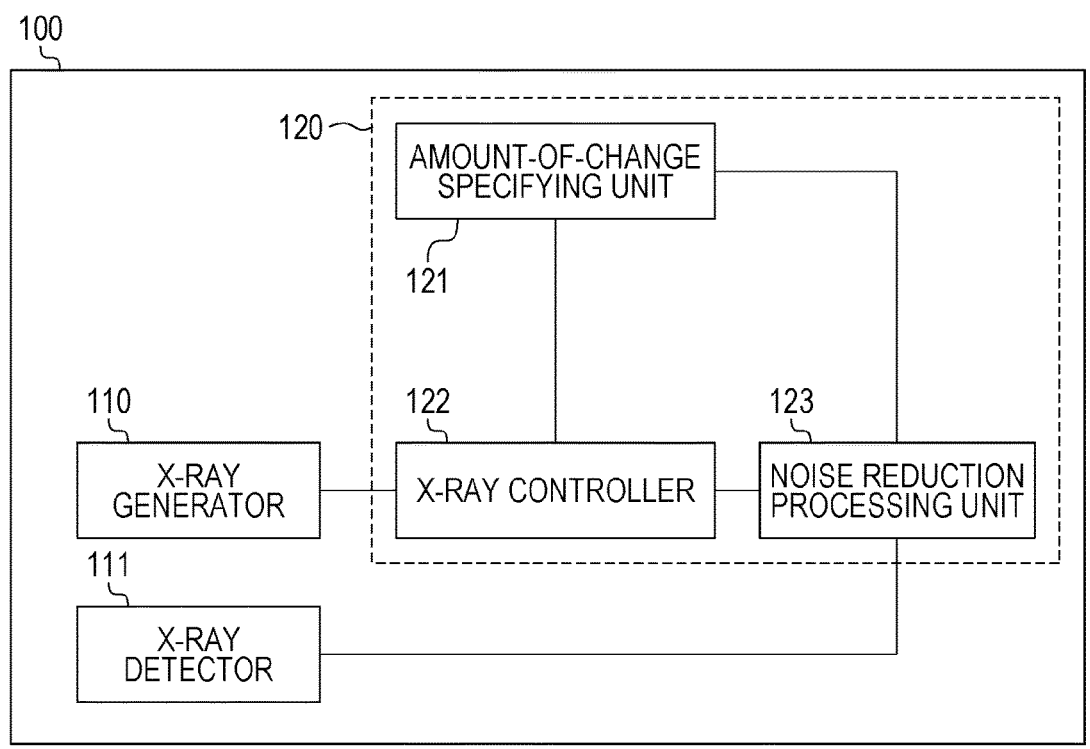
FIG. 1 is a diagram illustrating a radiation imaging apparatus.

FIG. 1 is a diagram illustrating a radiation imaging apparatus 100 according to a first embodiment. The radiation imaging apparatus 100 includes an X-ray generator 110, an X-ray detector 111, and a control device 120. The control device 120 includes an amount-of-change specifying unit 121, an X-ray controller 122, and a noise reduction processing unit 123.

The X-ray generator 110 emits X-rays (radiated rays) toward a patient serving as a subject. The X-ray detector 111 then detects X-rays that have passed through the patient, and generates image data on the basis of the detected X-rays. The X-ray detector 111 performs X-ray detection and image-data generation in a serial manner, and acquires a plurality of pieces of image data.

The radiation imaging apparatus 100 according to the present embodiment is able to change the relative position of the X-ray detector 111 with respect to the patient serving as the subject. Specifically, the radiation imaging apparatus 100 is provided with, in a movable manner, at least one of the X-ray detector 111 and a table (not illustrated) for placing a patient thereon.

Every time the X-ray detector 111 detects radiated rays and generates image data, a controller, which is not illustrated, moves the X-ray detector 111 or the table. As a result, the radiation imaging apparatus 100 is able to change the relative position as appropriate. Note that, under control performed by the controller, the X-ray generator 110 moves in accordance with the movement of the X-ray detector 111.

The amount-of-change specifying unit 121 specifies, every time image data is generated, the amount of change in the relative position during the period from a generation timing of immediately preceding image data to a generation timing of target image data. Here, the target image data is processing-target image data, and the immediately preceding image data is image data generated immediately before the target image data. Note that the amount-of-change specifying unit 121 specifies the amount of change in the relative position in accordance with, for example, the movement of the table on which a subject is placed, a retainer of the X-ray detector 111, a radiation-tube supporting column, a collimator, and the like.

As another example, the amount-of-change specifying unit 121 may specify the amount of change in the relative position in accordance with an analysis result of image data generated by the X-ray detector 111. Regarding a method for specifying the amount of change in a relative position in accordance with an analysis result of image data, for example, it is possible to refer to Japanese Patent Laid-Open No. 2008-220414.

Figure 2:
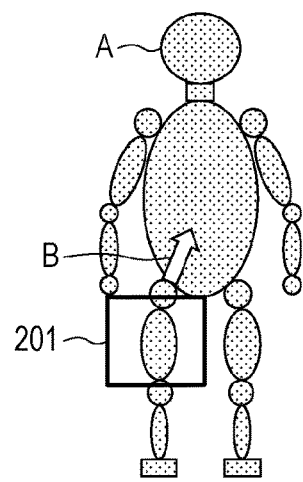
FIG. 2 is a diagram for describing processing performed to change a relative position.
Figure 2:
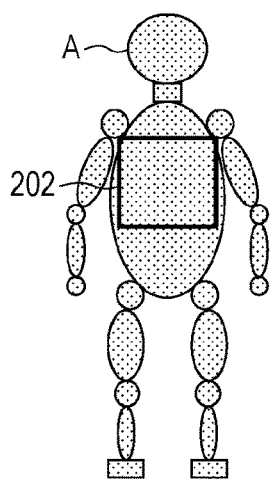
Figure 2:
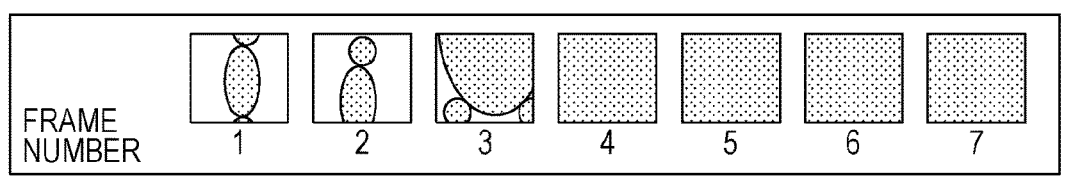

FIG. 2 is a diagram for describing processing performed to change a relative position. The relative position of the X-ray detector 111 with respect to a subject A changes along the direction of an arrow B from a position 201 illustrated in FIG. 2(a) to a position 202 illustrated in FIG. 2(b). At the position 202, the relative position of the X-ray detector 111 with respect to the subject A enters a state where the relative position is fixed, that is, a state where the field of view is fixed. In accordance with this, while the relative position is being changed from the position 201 to the position 202, the X-ray detector 111 performs imaging for image data as appropriate. Even after the relative position is fixed to the position 202, the X-ray detector 111 regularly performs imaging for image data.

FIG. 2(c) is a diagram illustrating an example of image data acquired in accordance with a change in the relative position illustrated in FIGS. 2(a) and (b). Image data having a frame number of 1 is image data corresponding to X-rays emitted at the position 201 of FIG. 2(a). Image data having frame numbers of 2 to 4 is image data corresponding to X-rays emitted while the relative position is being changed along the direction of the arrow B. Image data having a frame number of 4 is image data corresponding to X-rays emitted at the position 202 of FIG. 2(b). Image data having frame numbers of 5 to 7 is pieces of image data sequentially generated in a state where the relative position is fixed.

In this manner, the radiation imaging apparatus 100 is able to successively generate pieces of image data at regular time intervals. Furthermore, in a state where the relative position is fixed, the radiation imaging apparatus 100 is able to successively generate pieces of image data at regular time intervals. Note that the image-data generation intervals, that is, the imaging intervals may be freely determined. In addition, the imaging intervals do not have to be constant.

The X-ray controller 122 sets the amount of X-rays in accordance with the amount of change, which is specified by the amount-of-change specifying unit 121, in the relative position. The X-ray controller 122 then sets irradiation conditions such as a tube voltage, a tube current, and an irradiation time in accordance with the set amount of X-rays. The amount of X-rays set by the X-ray controller 122 is a target value for the amount of X-rays that have passed through a subject.

First, a process for setting the amount of X-rays in accordance with the amount of change in a relative position will be described. The X-ray controller 122 sets the amount of X-rays to 1 μGy (a first amount of X-rays) when the amount of change is smaller than or equal to an amount-of-change threshold value, and sets the amount of X-rays to 2 μGy (a second amount of X-rays) when the amount of change is larger than the amount-of-change threshold value.

Here, the amount-of-change threshold value is prestored in, for example, a ROM, which is described later. Note that, in the present embodiment, the amount-of-change threshold value is set to "0 mm".

That is, the X-ray controller 122 sets the first amount of X-rays in the case where a first amount of change is specified, while the X-ray controller 122 sets the second amount of X-rays in the case where a second amount of change is specified. Here, the second amount of change has a larger value than the first amount of change. The second amount of X-rays has a larger value than the first amount of X-rays.

Note that, in the present embodiment, the X-ray controller 122 treats an amount of change of "0 mm" as a change threshold value, and reduces the amount of X-rays from 2 μGy to 1 μGy in the case where the amount of change is smaller than or equal to an amount-of-change threshold value, which is "0 mm"; however, the amount-of-change threshold value is not limited to "0 mm", and may be any other value.

Next, a process for setting irradiation conditions will be described. Note that a process for setting the amount of X-rays will be described later. The X-ray controller 122 determines a tube voltage and a tube current in accordance with the amount of X-rays and by referring to a kV-mA table. Here, the kV-mA table is information in which the transmittance of a subject, and the tube voltage and tube current corresponding to the transmittance are defined on an amount-of-X-rays-by-amount-of-X-rays basis. The kV-mA table is preset in, for example, a ROM or the like.

Figure 3:
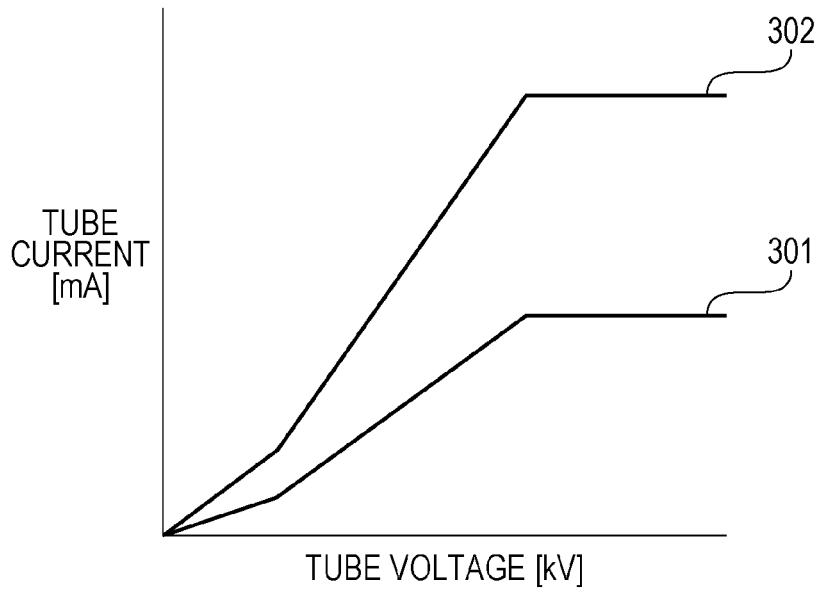
FIG. 3 is a diagram illustrating a graph into which kV-mA tables are converted.

FIG. 3 is a diagram illustrating a graph into which kV-mA tables are converted. In the graph of FIG. 3, the horizontal axis represents the tube voltage (kV), and the vertical axis represents the tube current (mV). In the graph, lines 301 and 302 represent kV-mA tables corresponding to the respective amounts, which differ from each other, of X-rays. The lines 301 and 302 are kV-mA tables corresponding to respective 1 μGy and 2 μGy.

The thicker the subject, the more difficult it becomes for radiated rays to pass through the subject. According to this, the lines 301 and 302 define sets of a tube-voltage value and a tube-current value such that the lower the transmittance, the higher at least one of a tube voltage and a tube current becomes.

The X-ray controller 122 selects, in accordance with the set amount of X-rays, either one of the kV-mA tables corresponding to the lines 301 and 302. The X-ray controller 122 then determines a tube-voltage value and a tube-current value in accordance with the transmittance of a subject. In this manner, the X-ray controller 122 is able to set appropriate irradiation conditions based on the thickness of the subject by referring to the kV-mA table.

Note that the X-ray controller 122 estimates a transit dose in accordance with the image data acquired by the X-ray detector 111. The X-ray controller 122 calculates a transmittance in accordance with the estimated transit dose and the amount of X-rays with which the subject is irradiated, and determines a tube-voltage value and a tube-current value in accordance with the transmittance.

Note that the process for estimating a transit dose is not limited to the embodiment. As another example, the radiation imaging apparatus 100 may also estimate a transit dose by using a device such as an automatic exposure control system.

The description refers to FIG. 1 again. The noise reduction processing unit 123 reduces, for target image data being treated as a processing target, the noise of the target image data by combining, with the target image data, a piece of image data that has already been acquired through a series of serial imaging acts. Specifically, the noise reduction processing unit 123 performs combining processing in accordance with the algorithm of recursive filtering. Recursive filtering is processing for multiplying target image data (the current frame) by a certain coefficient, multiplying image data (the preceding frame), which has already been generated, by a certain coefficient, and combining the resulting pieces of image data. Combining of a plurality of images in this manner makes it possible to remove a noise component, while the effect of an after image due to combining appear significantly in the case where a change in position is large.

The noise reduction processing unit 123 performs recursive filtering in accordance with (Eq. 1).

$$T_n = aS_n + (1-a)T_{(n-1)} \quad \text{(Eq. 1)}$$

Here, $T_n$ represents the current frame after noise reduction processing. $S_n$ represents image data (the current frame) acquired by the X-ray detector 111, that is, the current frame before the noise reduction. $T_{(n-1)}$ represents the immediately preceding frame after the noise reduction processing. In addition, a represents a recursive filter coefficient.

A recursive filter coefficient a represents a composition ratio of the current frame. Thus, the larger the recursive filter coefficient a, the higher the composition ratio of the current frame and the smaller the composition ratio of the preceding frame.

The noise reduction processing unit 123 determines, in accordance with the amount of change in the relative position specified by the amount-of-change specifying unit 121, the value of the recursive filter coefficient a to be used in noise reduction processing for the target image data. The noise reduction processing unit 123 determines the recursive filter coefficient a so that the larger the amount of change, the larger the value of the recursive filter coefficient a. That is, the noise reduction processing unit 123 determines the composition ratio of the preceding frame so that the larger the amount of change, the larger the composition ratio of the preceding frame (composition ratio determination processing).

Specifically, the noise reduction processing unit 123 refers to a correspondence table regarding the amount of change and the recursive filter coefficient a, and determines the recursive filter coefficient a in accordance with the amount of change. Here, the correspondence table is prestored in, for example, a ROM or the like.

That is, the noise reduction processing unit 123 determines a first composition ratio for the preceding frame in the case where a first amount of change is specified, while the noise reduction processing unit 123 determines a second composition ratio for the preceding frame in the case where a second amount of change is specified. Here, the second amount of change has a larger value than the first amount of change. The second composition ratio has a smaller value than the first composition ratio.

As another example, the noise reduction processing unit 123 may also determine the recursive filter coefficient a using a function that calculates the recursive filter coefficient a from the amount of change. In this case, the function is prestored in, for example, a ROM or the like.

Figure 4:
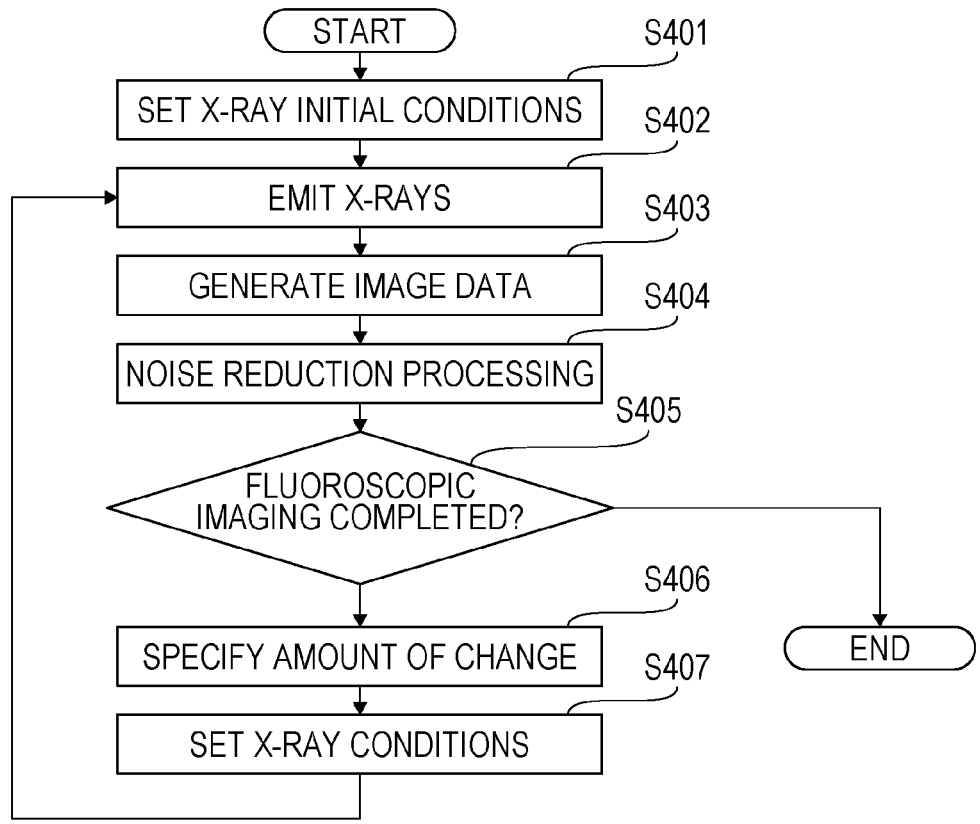
FIG. 4 is a flowchart illustrating an imaging process.

FIG. 4 is a flowchart illustrating an imaging process performed by the radiation imaging apparatus 100. The radiation imaging apparatus 100 acquires a series of serial pieces of image data in the imaging process. In step S401, the X-ray controller 122 sets initial conditions such as a tube voltage, a tube current, and an irradiation time. Initial conditions for respective apparatuses to be used, for respective portions whose images to be captured, and for respective types of examination are prestored in a ROM or the like. The X-ray controller 122 sets initial conditions corresponding to an apparatus to be used and the like.

In step S402, the X-ray generator 110 emits X-rays toward a subject under the irradiation conditions set in step S401 or step S407, which will be described later (irradiation processing). Next, in step S403, the X-ray detector 111 detects radiated rays that have passed through the subject, and generates image data in accordance with the detection result (detection processing, generation processing).

Next, in step S404, the noise reduction processing unit 123 acquires the image data (target image data) generated in step S403 (acquisition processing), and performs noise reduction processing (noise reduction processing) on the target image data. As a result, the image data acquired by the X-ray detector 111 is converted into an image suitable for diagnosis and examination.

Next, in step S405, the X-ray controller 122 confirms whether or not a series of serial image acts is completed. In the case where the serial imaging acts are completed (Yes in step S405), the X-ray controller 122 ends the imaging process.

In the case where the serial imaging acts are not completed (No in step S405), the X-ray controller 122 causes the process to proceed to step S406. In step S406, the amount-of-change specifying unit 121 specifies the amount of change in the relative position (amount-of-change specification processing). Next, in step S407, the X-ray controller 122 sets the amount of X-rays in accordance with the amount of change in the relative position (amount-of-radiated-rays setting processing), sets irradiation conditions in accordance with the amount of X-rays, and causes the process to proceed to step S402.

Figures 5, 6, 7, 8:
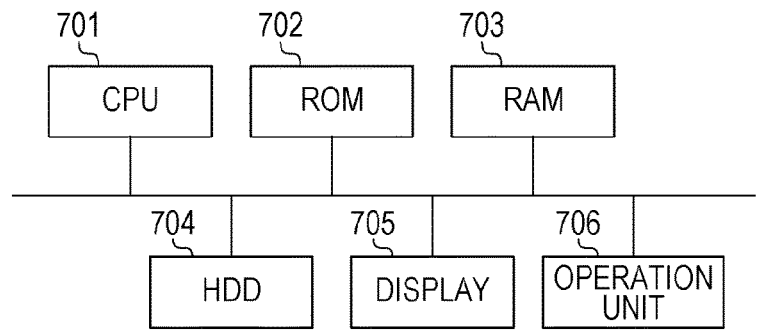
FIG. 5 is a diagram illustrating amount-of-X-rays setting values.
FIG. 6 is a diagram illustrating a recursive filter coefficient.
FIG. 7 is a diagram illustrating a computer.
FIG. 8 is a diagram illustrating amount-of-X-rays setting values.

FIG. 5 is a diagram illustrating image data (frames) generated in the imaging process, the amounts of change in the relative position, and amount-of-X-rays setting values. The amounts of change in the relative position are values specified by the amount-of-change specifying unit 121. The amount-of-X-rays setting values are the amounts of X-rays set by the X-ray controller 122. The example illustrated in FIG. 5 corresponds to FIG. 2(*c*), and the amount of change is smaller than or equal to "0 mm", which is the amount-of-change threshold value, at the fifth frame. In accordance with this, the X-ray controller 122 increases the amount of X-rays from "2 µGy" to "1 µGy" at the fifth frame.

Note that in the present embodiment, the irradiation conditions for the sixth frame are changed in accordance with the amount of change obtained at the fifth frame. Thus, the data to which a change made to the irradiation conditions ("1 µGy" as the amount-of-X-rays setting value) is actually applied is the image data obtained at and after the sixth frame.

In the case where the amount of change in the relative position is small, that is, the shift of the field of view has become small, the degree of image degradation caused by a shift in position is small even when the composition ratio of the preceding frame is made larger than that of the current frame in recursive filtering. Furthermore, in the case where the composition ratio of the preceding frame is increased, high-quality image data may be acquired even when the amount of X-rays is reduced for the current frame. In addition, in the case where the amount of change is small, high-quality image data may be acquired because of the effect of the persistence of vision even when the amount of X-rays is reduced.

From the foregoing, the X-ray controller 122 reduces the amount of X-rays when the amount of change in the relative position becomes smaller than or equal to the amount-of-change threshold value. As a result, the radiation imaging apparatus 100 is able to reduce the amount of radiated rays to which the subject is exposed, while maintaining the quality of image data to be generated.

FIG. 6 is a diagram illustrating image data (frames) generated in the imaging process, the amounts of change in the relative position, and the recursive filter coefficient a. FIG. 6 corresponds to FIG. 2(c), and the amount of change in the relative position becomes "0" at the fifth frame. In accordance with this, the noise reduction processing unit 123 reduces the recursive filter coefficient from "0.8" to "0.5" at the fifth frame.

In this manner, the smaller the amount of change in the relative position, the more the noise reduction processing unit 123 reduces the recursive filter coefficient a, so that the composition ratio of the preceding frame is made larger than that of the current frame. Thus, the noise reduction processing unit 123 is able to reduce noise while suppressing the effect of an after image.

As described above, the radiation imaging apparatus 100 according to the present embodiment determines, in accordance with the amount of change in the relative position, an amount-of-X-rays setting value and the composition ratio of the frame preceding the current frame in recursive filtering. As a result, high-quality image data may be acquired, while the amount of radiated rays to which a patient is exposed is reduced.

FIG. 7 is a diagram illustrating a hardware configuration of the control device 120. The control device 120 includes a CPU 701, a ROM 702, a RAM 703, a HDD 704, a display 705, and an operation unit 706. The CPU 701 reads out a control program stored in the ROM 702, and executes various types of processing. The RAM 703 is used as a temporary storage area such as a main memory of the CPU 701, a work area, and the like. The HDD 704 stores image data, various types of program, various types of information to be described later, and the like. The display 705 displays various types of information. The operation unit 706 receives various types of operation from an operator.

The functions of the control device 120 described with reference to FIG. 1 are realized by the CPU 701 reading out a program stored in the ROM 702 or the HDD 704 and executing this program. Likewise, a process performed by the control device 120 and described with reference to FIG. 4 is realized by the CPU 701 reading out a program stored in the ROM 702 or the HDD 704 and executing this program.

Next, a first modification of the radiation imaging apparatus 100 according to the present embodiment will be described. As the first modification, the radiation imaging apparatus 100 may further include a motion detection unit. The motion detection unit detects motion in accordance with image data, and separates the image data into a motion-detected region where motion is detected and a no-motion-detected region where no motion is detected. The noise reduction processing unit 123 combines spatial filters such as a recursive filter, a smoothing filter, and the like, and performs processes appropriate for the respective regions on a region-by-region basis. In this manner, the noise reduction processing unit 123 is able to perform more optimized noise reduction processing by performing an analysis in accordance with the algorithm of noise reduction processing.

As a second modification, the radiation imaging apparatus 100 may change the sensitivity of the X-ray detector 111 or perform pixel-value correction on acquired image data in the case where the amount of X-rays is changed by the X-ray controller 122. This is because the amount of X-rays reaching the X-ray detector 111 becomes different in the case where the amount-of-X-rays setting value is changed. The radiation imaging apparatus 100 is able to acquire constant pixel values regardless of the amount-of-X-rays setting value by, for example, changing the sensitivity of the X-ray detector 111. In addition, in the case where the tube voltage is changed, image contrast changes. Thus, as another example, the radiation imaging apparatus 100 may also perform contrast correction on the image data.

As a third modification, instead of selecting a kV-mA table, the X-ray controller 122 may adjust at least one of the irradiation time, the tube current, and the tube voltage in accordance with fluoroscopic conditions of the preceding frame (adjustment processing). As a result, the X-ray controller 122 is able to change the amount of X-rays without changing a kV-mA table.

Second Embodiment

Next, a radiation imaging apparatus 100 according to a second embodiment will be described. Here, regarding the radiation imaging apparatus 100 according to the second embodiment, portions that differ from the radiation imaging apparatus 100 according to the first embodiment will be described.

FIG. 8 is a diagram illustrating image data (frames) generated in an imaging process, the amounts of change in the relative position, and amount-of-X-rays setting values. In the second embodiment, the X-ray controller 122 increases the amount of X-rays from "1 µGy" to "2 µGy" at the fifth frame (amount-of-radiated-rays change processing). Furthermore, the X-ray controller 122 reduces the amount of X-rays from "2 µGy" to "1 µGy" at the sixth frame.

The X-ray controller 122 changes, in accordance with the changed amount of X-rays, irradiation conditions to be used at the time of the next irradiation. In the case where the amount-of-X-rays setting value is changed at the fifth frame, the X-ray controller 122 changes irradiation conditions for the sixth frame. In the example illustrated in FIG. 8, in accordance with the irradiation conditions for the fifth frame, the X-ray controller 122 changes the tube voltage, the tube current, the irradiation time, and the like so that the amount of X-rays becomes a desired value.

FIG. 9 is a diagram illustrating image data (frames) generated in the imaging process, the amounts of change in the relative position, and the recursive filter coefficient a. The noise reduction processing unit 123 increases the recursive filter coefficient a for the first to sixth frames, whose amount-of-X-rays setting values are small, and reduces the recursive filter coefficient a at the seventh frame, whose amount-of-X-rays setting value is large. Reduction of the recursive filter coefficient a at the seventh frame means that the composition ratio of the sixth frame is increased.

Note that, in the case where the amount of change in the relative position is increased again at and after the eighth frame subsequent to the seventh frame, the noise reduction processing unit 123 increases the recursive filter coefficient a again.

That is, in the present embodiment, the X-ray controller 122 temporarily changes the amount of X-rays to a large value (a second amount of radiated rays) in the case where the amount of change in the relative position is changed from a value larger than the amount-of-change threshold value to a value smaller than or equal to the amount-of-change threshold value.

Then, the noise reduction processing unit 123 increases the composition ratio of image data generated at the timing at which the amount of change in the relative position is changed from the value larger than the amount-of-change threshold value to the value smaller than or equal to the amount-of-change threshold value. As a result, the radiation imaging apparatus 100 is able to effectively reduce noise.

Furthermore, the X-ray controller 122 reduces the amount of X-rays again when a certain period of time passes after the amount of X-rays is changed to the large value. As a result, the radiation imaging apparatus 100 is able to reduce the amount of radiated rays to which a patient is exposed. In addition, the radiation imaging apparatus 100 sets the amount-of-X-rays setting value to a low value (1 µGy) in the case where the amount of change is larger than the amount-of-change threshold value as at the first to fifth frames illustrated in FIG. 7. As a result, the amount of radiated rays to which a patient is exposed may be reduced.

Note that the configuration of and the process performed by the radiation imaging apparatus 100 according to the second embodiment other than this are similar to the configuration of and the process performed by the radiation imaging apparatus 100 according to the first embodiment.

As described above, the radiation imaging apparatus 100 according to the second embodiment temporarily increases the amount of X-rays in the case where the amount of change in the relative position becomes small, and performs noise reduction processing using image data corresponding to this amount of X-rays. As a result, high-quality image data may be acquired, while the amount of radiated rays to which a patient is exposed is reduced.

In this manner, in the case where the amount of change in the relative position is larger than the amount-of-change threshold value, processing for reducing the amount-of-X-rays setting value is, for example, processing appropriate for such a case where, for example at the time when a table on which a patient is placed is moved, image data of certain quality high enough to roughly identify portions to be imaged needs to be acquired.

A modification of the radiation imaging apparatus 100 according to the second embodiment will be described. The radiation imaging apparatus 100 according to the modification may perform edge-preservation-type spatial filtering on image data for which the amount of X-rays is large, and thereafter perform recursive filtering on the resulting image data. An image for which the amount of X-rays is large has a high SN ratio. Consequently, the radiation imaging apparatus 100 is able to separate noise from a configuration with relatively high accuracy. The radiation imaging apparatus 100 is thus able to acquire image data with noise that is further suppressed, by performing edge-preservation-type spatial filtering.

Third Embodiment

Next, the radiation imaging apparatus 100 according to a third embodiment will be described. Here, regarding the radiation imaging apparatus 100 according to the third embodiment, portions that differ from the radiation imaging apparatuses 100 according to the other embodiments will be described. An X-ray controller 122 according to the third embodiment stores, in a ROM or the like, image data of the sixth frame, as a key frame, at which the amount of change in the relative position becomes small and that is acquired in accordance with a large amount of X-rays. Here, the key frame is an example of reference image data. The noise reduction processing unit 123 then performs, on target image data, recursive filtering such that the key frame is combined with the target image data.

Specifically, the noise reduction processing unit 123 performs recursive filtering expressed by (Eq. 2).

$$T_n = aS_n + (1-a)T_{key} \quad \text{(Eq. 2)}$$

Here, $T_n$ represents the current frame after noise reduction processing. $S_n$ represents image data (the current frame) acquired by the X-ray detector 111, that is, the current frame before the noise reduction. $T_{key}$ represents a key image. In addition, a represents a recursive filter coefficient.

FIG. 10 is a diagram illustrating image data (frames) generated in an imaging process, the amounts of change in the relative position, and amount-of-X-rays setting values. As illustrated in FIG. 10, the X-ray controller 122 increases the amount of X-rays at the fifth frame at which the amount of change in the relative position becomes smaller than or equal to the amount-of-change threshold value. In accordance with this, the irradiation conditions for image data of the sixth frame are changed.

Furthermore, after increasing the amount of X-rays for the six frame, the X-ray controller 122 reduces the amount of X-rays at the seventh frame at which the amount of change in the relative position stays smaller than or equal to the amount-of-change threshold value. Note that, as another example, in the case where the amount of change in the relative position becomes smaller than or equal to the threshold, the amount of X-rays may be made to stay thereafter at an increased value for a period corresponding to predetermined frames.

The X-ray controller 122 stores, in a memory, the sixth frame, as a key frame, captured when the amount-of-X-rays setting value is "2". The noise reduction processing unit 123 then performs, on image data of the seventh and subsequent frames, recursive filtering using the key frame. Note that, in the present embodiment, the recursive filter coefficient has a constant value. As a result, the amount of noise may be maintained constant. The recursive filter coefficient is pre-stored in a ROM or the like.

Note that in the case where the amount of change in the relative position becomes larger than the amount-of-change threshold value again, the X-ray controller 122 deletes the key frame from the memory. For generated image data, processing for combining, with the generated image, image data that has already been generated is not performed. Note that the configuration of and the process performed by the radiation imaging apparatus 100 according to the third embodiment other than this are similar to the configurations of and the processes performed by the radiation imaging apparatuses 100 according to the other embodiments.

In this manner, in the third embodiment, the noise reduction processing unit 123 combines the key frame, which is captured when the amount-of-X-rays setting value is high and which includes a small amount of noise, with the current frame. Thus, noise may be effectively reduced.

As a first modification of the radiation imaging apparatus 100 according to the third embodiment, the X-ray controller 122 may combine a plurality of pieces of image data having a small amount of noise, generate one key frame, and store this key frame in a memory.

As a second modification, instead of using a constant value as the recursive filter coefficient, the noise reduction processing unit 123 may use a recursive filter coefficient such that the composition ratio of the key frame is reduced in accordance with a time period that has passed from the generation timing of the key frame. As a result, a shift in position between the current frame and the key frame may be prevented from occurring.

As another example, in terms of prevention of a shift in position from occurring, the noise reduction processing unit 123 may correct a shift in position between the current frame and the key frame in accordance with a time period that has passed from the generation timing of the key frame, and combine the key frame with the current frame.

Next, a third modification will be described. Regarding the radiation imaging apparatus 100, there may be a case where a catheter or the like is inserted into the body of a patient at a timing at which the amount of change in the relative position becomes smaller than or equal to the threshold (at and after the fifth frame in FIG. 10). In the case where a catheter or the like is inserted, the radiation imaging apparatus 100 according to the third modification separates image data into an inserted-object region corresponding to the catheter, and a non-inserted-object region corresponding to objects other than the catheter.

Specifically, the radiation imaging apparatus 100 performs separation into the inserted-object region and the non-inserted-object region by comparing pixel values of target image data and those of image data acquired immediately before the target image data, performing recognition processing for a configuration on a line, performing motion detection in image data (motion detection processing), and the like.

The noise reduction processing unit 123 performs recursive filtering on the inserted-object region and the non-inserted-object region using recursive filter coefficients that differ from each other. Specifically, the noise reduction processing unit 123 performs recursive filtering on the non-inserted-object region, where a change in image data is small, using a low recursive filter coefficient.

In contrast, the noise reduction processing unit 123 performs recursive filtering on the inserted-object region, where a change in image data is large, using a recursive filter coefficient higher than the recursive filter coefficient of the non-inserted-object region. As a result, recognizability of a catheter may be improved in image data.

As a fourth modification, in the case where a state continues where the amount of change in the relative position is small, the X-ray controller 122 increases the amount of X-rays again every time a certain period of time passes or every time generation of a certain number of frames is completed. The X-ray controller 122 then replaces the key frame, which has been prestored, with image data generated in accordance with a large amount of X-rays. As a result, a shift in position corresponding to a time period that has passed may be prevented from occurring.

Note that the imaging process performed by the radiation imaging apparatus 100 according to the present embodiment may be executed in a selective manner. The imaging process according to the present embodiment is not suitable for imaging of a portion such as a heart where motion is regularly detected. Thus, the imaging process according to the present embodiment may be executed only when images of a certain portion are captured. In addition, as another example, the imaging process according to the present embodiment may be executed in the case where certain imaging conditions are selected.

Other Embodiments

In addition, the present invention is realized also by executing the following processing. That is, software (a program) that realizes the functions of the above-described embodiments is supplied to a system or an apparatus via a network or various types of storage medium. The processing is processing in which a computer (or a CPU, an MPU, or the like) of the system or apparatus reads out and executes the program.

According to the embodiments described above, high-quality image data may be acquired, while the amount of radiated rays to which a patient is exposed is reduced.

Preferred embodiments of the present invention are described above in detail. The present invention is not limited to these specific embodiments, and various modifications and changes are possible within the scope of the gist of the present invention described in claims.

This application claims for priority on the basis of Japanese Patent Application No. 2013-232310 filed Nov. 8, 2013, which is hereby incorporated by reference herein in its entirety.

REFERENCE SIGNS LIST 100 radiation imaging apparatus
110 X-ray generator
111 X-ray detector
120 control device
121 amount-of-change specifying unit
122 X-ray controller
123 noise reduction unit

The invention claimed is:

1. A control device comprising:
a memory storing a program; and
one or more processors which, by executing the program, function as:
an amount-of-change specifying unit configured to specify, among a plurality of pieces of image data generated by a detection unit in accordance with a detection result of radiated rays that have passed through a subject, the amount of change in a relative position of the subject with respect to the detection unit during a period from a generation timing of first image data, which is generated immediately before second image data, to a generation timing of the second image data;
an amount-of-radiated-rays setting unit configured to set a first amount of radiated rays in a case where the amount of change is larger than an amount-of-change threshold value, set a second amount of radiated rays larger than the first amount of radiated rays in a case where the amount of change is changed from a value larger than the amount-of-change threshold value to a value smaller than or equal to the amount-of-change threshold value;
a composition ratio determination unit configured to determine a composition ratio of the second image data generated in accordance with irradiation of the second amount of radiated rays to a value larger than a composition ratio of the first image data generated before the second image data corresponding to the irradiation of the second amount of radiated rays at a timing at which the amount of change is changed from the value larger than the amount-of-change threshold value to the value smaller than or equal to the amount-of-change threshold value; and
a combining processing unit configured to combine, by performing recursive filtering in accordance with the composition ratio, the first image data generated before the second image data with the second image data.

2. The control device according to claim 1, wherein
the amount-of-radiated-rays setting unit is configured to set the first amount of radiated rays after a certain period of time has passed after setting of the second amount of radiated rays.

3. The control device according to claim 1, wherein the one or more processors further function as an adjustment unit configured to adjust at least one value among a tube voltage, a tube current, and an irradiation time in accordance with the amount of radiated rays.

4. An imaging apparatus comprising:
the control device according to claim 1;
an irradiation unit configured to perform irradiation with radiated rays;
a generation unit configured to detect, in a serial manner, radiated rays that have passed through the subject, and generate a plurality of pieces of image data in accordance with detection results.

5. A control device comprising:
a memory storing program; and
one or more processors which, by executing the program, function as:
an amount-of-change specifying unit configured to specify, among a plurality of pieces of image data generated by a detection unit in accordance with radiated rays that have passed through a subject, the amountof change in a relative position of the subject with respect to the detection unit during a period from a generation timing of first image data, which is generated immediately before second image data, to a generation timingof the second image data;
ana mount-of-radiated-rays setting unit configured to change a first amount of radiated rays to a second amount of radiated rays larger than the first amount of radiated rays in a case where the amount of change is changed from a value larger than an amount-of-change threshold value to a value smaller than or equal to the amount-of-change threshold value; and
combining processing unit configured to combine, by peforming recursive filtering in accordance with a composition ratio larger than a composition ratio in a case where the amount of change is larger than the amount-of-change threshold value, the first image data generated in accordance with irridiation of the second amount of radiated rays with the second image data in a case where the amount of change is changed from a value larger than the amount-of-change threshold value to a value smaller than or equal to the amount-of-change threshold value.

6. The control device according to claim 5,
wherein the amount-of-radiated-rays setting unit changes the second amount of radiated rays to a third amount of radiated rays smaller than the second amount of radiated rays in a case where a predetermined period elapses after the amount-of-radiated-rays setting unit changes the first amount of radiated rays.

7. The control device according to claim 6, wherein the third amount of radiated rays is equal to the first amount of radiated rays.

8. A control method, the control method being executed by a control device, comprising:
specifying, among a plurality of pieces of image data generated by a detection unit in accordance with a detection result of radiated rays that have passed through a subject, an amount of change in a relative position of the subject with respect to the detection unit during a period from a generation timing of first image data, which is generated immediately before second image data, to a generation timing of the second image data;

setting a first amount of radiated rays in a case where the amount of change is larger than an amount-of-change threshold value, setting a second amount of radiated rays larger than the first amount of radiated rays in a case where the amount of change is changed from a value larger than the amount-of-change threshold value to a value smaller than or equal to the amount-of-change threshold value;

determining a composition ratio of the second image data generated in accordance with irradiation of the second amount of radiated rays to a value larger than a composition ratio of the first image data generated before the second image data corresponding to the irradiation of the second amount of radiated rays at a timing at which the amount of change is changed from the value larger than the amount-of-change threshold value to the value smaller than or equal to the amount-of-change threshold value; and combining, by performing recursive filtering in accordance with the composition ratio, the first image data generated before the second image data with the second image data.

9. A control method, the control method being executed by a control device, comprising:
specifying, among a plurality of pieces of image data generated by a detection unit in accordance with radiated rays that have passed through a subject, an amount of change in a relative position of the subject with respect to the detection unit during a period from a generation timing of first image data, which is generated immediately before second image data, to a generation timing of the second image data;

changing a first amount of radiated rays to a second amount of radiated rays larger than the first amount of radiated rays in a case where the amount of change is changed from a value larger than an amount-of-change threshold value to a value smaller than or equal to the amount-of-change threshold value; and combining, by performing recursive filtering in accordance with a composition ratio larger than a composition ratio in a case where the amount of change is larger than the amount-of-change threshold value, the first image data generated in accordance with irradiation of the second amount of radiated rays with second image data in a case where the amount of change is changed from a value larger than the amount-of-change threshold value to a value smaller than or equal to the amount-of-change threshold value.

10. The control method according to claim 9,
wherein the second amount of radiated rays is changed to a third amount of radiated rays smaller than the second amount of radiated rays in a case where a predetermined period elapses after the first amount of radiated rays is changed to the second amount of radiated rays.

11. A non-transitory storage medium containing program instructions for causing a computer to function as:
an amount-of-change specifying unit configured to specify, among a plurality of pieces of image data generated by a detection unit in accordance with a detection result of radiated rays that have passed through a subject, the amount of change in a relative position of the subject with respect to the detection unit during a period from a generation timing of first image data, which is generated immediately before second image data, to a generation timing of the second image data;

an amount-of-radiated-rays setting unit configured to set a first amount of radiated rays in a case where the amount of change is larger than an amount-of-change threshold value, set a second amount of radiated rays larger than the first amount of radiated rays in a case where the amount of change is changed from a value larger than the amount-of-change threshold value to a value smaller than or equal to the amount-of-change threshold value;

a composition ratio determination unit configured to determine a composition ratio of the second image data generated in accordance with irradiation of the second amount of radiated rays to a value larger than a composition ratio of the first image data generated before the second image data corresponding to the irradiation of the second amount of radiated rays at a timing at which the amount of change is changed from the value larger than the amount-of-change threshold value to the value smaller than or equal to the amount-of-change threshold value; and a combining processing unit configured to combine, by performing recursive filtering in accordance with the composition ratio, the first image data generated before the second image data with the second image data.

12. A non-transitory storage medium containing program instructions for causing a computer to function as:

an amount-of-change specifying unit configured to specify, among a plurality of pieces of image data generated by a detection unit in accordance with radiated rays that have passed through a subject, the amount of change in a relative position of the subject with respect to the detection unit during a period from a generation timing of first image data, which is generated immediately before second image data, to a generation timing of the second image data;

an amount-of-radiated-rays setting unit configured to change a first amount of radiated rays to a second amount of radiated rays larger than the first amount of radiated rays in a case where the amount of change is changed from a value larger than an amount-of-change threshold value to a value smaller than or equal to the amount-of-change threshold value; and a combining processing unit configured to combine, by performing recursive filtering in accordance with a composition ratio larger than a composition ratio in a case where the amount of change is larger than the amount-of-change threshold value, the first image data generated in accordance with irradiation of the second amount of radiated rays with the second image data in a case where the amount of change is changed from a value larger than the amount-of-change threshold value to a value smaller than or equal to the amount-of-change threshold value.

13. The non-transitory storage medium according to claim 12, wherein the amount-of-radiated-rays setting unit changes the second amount of radiated rays to a third amount of radiated rays smaller than the second amount of radiated rays in a case where a predetermined period elapses after the amount-of-radiated-rays setting unit changes the first amount of radiated rays to the second amount of radiated rays.

* * * * *